(12) United States Patent
Nakajima et al.

(10) Patent No.: US 7,371,842 B2
(45) Date of Patent: May 13, 2008

(54) POLYNUCLEOTIDE ENCODING A 35 KDA PROTEIN THATS BINDS TO WF00144

(75) Inventors: Hidenori Nakajima, Osaka (JP); Mitsuru Ohkubo, Osaka (JP); Seiji Yoshimura, Osaka (JP); Nobuya Nishio, Osaka (JP); Kaori Nishio, Tsukuba-gun (JP)

(73) Assignee: Astellas Pharma Inc., Tokyo (JP)

( * ) Notice: Subject to any disclaimer, the term of this patent is extended or adjusted under 35 U.S.C. 154(b) by 0 days.

(21) Appl. No.: 10/511,270

(22) PCT Filed: Apr. 28, 2003

(86) PCT No.: PCT/JP03/05431

§ 371 (c)(1),
(2), (4) Date: May 23, 2005

(87) PCT Pub. No.: WO03/091436

PCT Pub. Date: Nov. 6, 2003

(65) Prior Publication Data

US 2005/0214858 A1  Sep. 29, 2005

(30) Foreign Application Priority Data

Apr. 26, 2002 (JP) .............................. 2002-126107

(51) Int. Cl.
*C07H 21/04* (2006.01)
*C12P 21/06* (2006.01)
*C12N 15/00* (2006.01)
*C07K 14/00* (2006.01)

(52) U.S. Cl. .................... 536/23.5; 536/23.1; 435/69.1; 435/320.1; 435/253.1; 530/300; 530/350

(58) Field of Classification Search ............... 536/23.1, 536/23.5; 435/69.1, 320.1, 252.3; 530/300, 530/350; 514/2
See application file for complete search history.

(56) References Cited

U.S. PATENT DOCUMENTS

2004/0219521 A1* 11/2004 Tang et al. ..................... 435/6

FOREIGN PATENT DOCUMENTS

| WO | 99/61645 | 12/1999 |
|---|---|---|
| WO | WO 99/61645 A | 12/1999 |
| WO | WO 0049134 A1 * | 8/2000 |
| WO | 02/46385 | 6/2002 |
| WO | WO 02/46385 A | 6/2002 |
| WO | WO 03/054152 | 7/2003 |

OTHER PUBLICATIONS

Carninci, P. and Hayashizaki, 1999, Meth. Enzymol., 303, 19-44.*
Carninci, P., Shibata, Y., Hayatsu, N., Sugahara, Y., Shibata, K., Itoh, M., Konno, H., Okazaky, Y., Muramatsu, M. and Hayashizaki, Y., 2000, Genome Res., 10(10), 1617-1630.*
Strausberg et al., Generation and Initial Analysis of More than 15,000 Full-length Human and Mouse cDNA Sequences, Dec. 2002, vol. 99, pp. 16899-16903.*
Database EMBL, Dec. 1, 2001, XP002401616.
Database EMBL, Nov. 5, 2001, XP002401617.
Strausberg, R. L., et al., "Generation and Initial analysis of more than 15,000 full-length human and mouse cDNA sequences", NCBI, Dec. 24, 2002, XP002245204.
Database EMBL, Jun. 1, 2001, XP002401618.
Database EMBL, Jan. 19, 2002, XP002401619.
Carninci, P. et al., High-efficiency full-length CDNA Cloning, Methods in Enzymology, Academic Press Inc., San Diego, CA, US, vol. 303, 1999, pp. 19-44.
Database EPO Proteins, Jan. 15, 2004, "Sequence 7483 from Patent EP1104808", XP002401620.
Database EMBL EST, sequence from *Homo sapiens*, Sep. 27, 2001, XP002401621.
Database EMBL EST, sequence from *Homo sapiens*, Sep. 27, 2001, XP002401622.
Database EMBL, Jun. 1, 2003, XP002401623.
Database Geneseq, Jan. 29, 2004, "Novel protein (useful for identifying genetic disorders) #227." XP002401624.
Kawai, J. et al. "Functional annotation of a full-length mouse cDNA collection", Nature, vol. 409, No. 6821, pp. 685-690 2001.
Strausberg, R.L. et al. "Generation and initial analysis of more than 15,000 full-length human and mouse cDNA sequences", PNAS, vol. 99, No. 26, pp. 16899-16903 2002.

* cited by examiner

*Primary Examiner*—Jon Weber
*Assistant Examiner*—Rita Mitra
(74) *Attorney, Agent, or Firm*—Oblon, Spivak, McClelland, Maier & Neustadt, P.C.

(57) ABSTRACT

It is intended to provide a protein participating in the regulation of sugar production, a polynucleotide encoding the same, a method of screening a compound participating in the regulation of sugar production and a drug for treating or preventing diabetes which contains the compound participating in the regulation of sugar production. A polynucleotide encoding a protein specifically binding to a substance WF00144 is found out from rat liver cells and thus a protein participating in the regulation of sugar production and a polynucleotide encoding the same are provided. Moreover, a method and a substance relating to a method of treating and preventing diabetes are found out and thus a method of treating diabetes relating to the regulation of sugar production relating to the method of treating and preventing diabetes is provided.

14 Claims, 1 Drawing Sheet

1
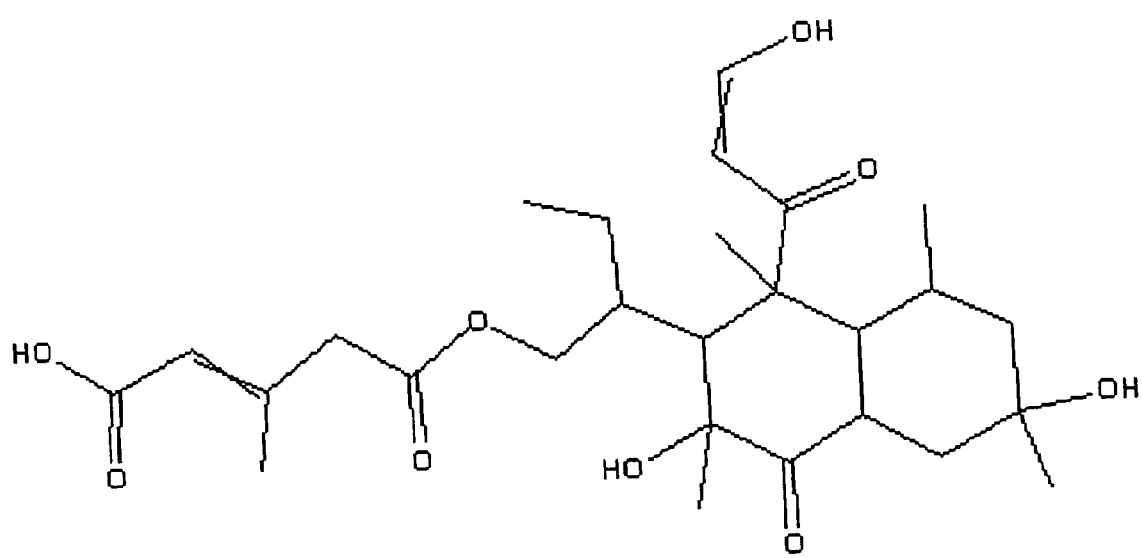

POLYNUCLEOTIDE ENCODING A 35 KDA PROTEIN THATS BINDS TO WF00144

TECHNICAL FIELD

The present invention relates to a novel 35 kd protein, a polynucleotide encoding the protein, a method for producing the protein by the use of the polynucleotide, as well as to an expression system relating to the production of these, and to a screening method for a compound participating in the regulation of sugar production by the use of the expression system.

The invention also relates to a method of treatment and prevention of diabetes by the use of the protein obtained according to the above-mentioned method or the compound obtained through screening.

BACKGROUND ART

The pharmaceutical effect of a drug that has a specific pharmaceutical activity and therefore expresses an effect of curing a disease of a type results from the specific binding of the drug to the protein that participates in the pharmaceutical phenomenon to carry the disease and from the effect of the drug caused by it to specifically modify the function of the protein.

Therefore, when a drug for curing a disease specifically binds to a protein to modify its function in tissues or cells that exhibit the disease, then the protein participates in the disease, and it is a useful target for development of new medicines for the disease.

For example, an immunosuppressor FK506 is used as a medicine for transplantation and chronic inflammations. Professor Schreiber et al. have clarified that the specific binding protein in the diseases to which the medicine is directed is FKBP12 protein (Harding M W, Galat A. Uehling D E, Schreiber S L, Nature 341, pp. 758-760 (1989)). It has been further clarified that, after FK506 has bound to FKBP12, this further binds to calcineurin to express its immunosuppressive effect (Liu J, Farmer J D Jr, Lane W S, Friedman J, Weissman I, Schreiber S L, Cell 66(4), pp. 807-815 (1991)). Specifically, FKBP12 discovered by the use of FK506 and its immunoregulation route are important targets for further development of additional immunosuppressors.

The novel 35 kd protein of the invention binds to a substance WF00144 (FIG. 1). The substance WF00144 is a pharmaceutically active substance produced by fungi, *Phoma* sp. No. 00144. This substance inhibits in-vitro sugar production in primary-culture liver cells. In addition, the substance has hypoglycemic effect in diabetes model animals. Specifically, the substance is a medicine for diabetes, which inhibits sugar production in livers and expresses hypoglycemic effect (WO99/61645).

For the two reasons mentioned above, it is believed that the protein to which the substance WF00144 specifically binds may be useful for clarifying some new mechanism for development of diabetes and for developing novel medicines for diabetes. Prior to the present invention, however, no one knows such a protein capable of specifically binding to the substance WF00144.

DISCLOSURE OF THE INVENTION

The theme of the invention includes the following three:

To provide a protein that participates in the regulation of sugar production, and to provide a polynucleotide that encodes it.

To provide a screening method for a compound that participates in the regulation of sugar production.

To provide a medicine that contains a compound participating in the regulation of sugar production and is for treatment or prevention of diabetes.

The invention provides a protein that participates in the regulation of sugar production and a polynucleotide that encodes it, and, by finding out a method or a substance for treatment and prevention of diabetes, provides a method for treatment of diabetes that participates in the regulation of sugar production relating to a method for treatment and prevention of diabetes.

We, the present inventors have assiduously studied and, as a result, have found out a polynucleotide that encodes a protein having a molecular weight of about 35 kd and participating in the regulation of sugar production, from rat liver cells, and have completed the present invention.

From rat liver cells, we have tried identification of a protein that specifically binds to the substance WF00144 having the ability to inhibit gluconeogenesis in primary-culture liver cells, and isolation of a gene that encodes the protein. As a result, we have identified a novel protein having a molecular weight of about 35 kd. From the partial sequence information of the protein, we have isolated a full-length gene. The gene has 96% homology to a Riken mouse clone 060010D20 on the level of amino acids, and it may be a homologous gene to the clone. However, its function is quite unknown.

In addition, we have isolated a human homologous gene. We have expressed the protein gene in *E. coli*, and have obtained a protein having a suitable molecular weight that is anticipated from the amino acid sequence thereof. The protein specifically rebinds to the substance WF00144.

In the BLAST homology search of the 35 kd protein of the invention, various biological homologues of the dihydrodipicolonate synthase (DHDPS) family account for the major part of the proteins. Accordingly, it is presumed that the rat and human 35 kd protein is a protein of the DHDPS family.

The motif search in the amino acid sequence of the 35 kd protein from the PROSITE database has revealed that the amino acid sequence contains two motifs stored in the DHDPS family. Of these, the sequence that contains an active center lysine, DHDPS_2(PROSITE AC.PS00666)Y-[DNS]-[LIVMFA]-P-x(2)-[ST]-x(3)-[LIVMF]-x(13,14)-[LIVM]-x-[SGA]-[LIVMF]-K-[DEQAF]-[STAC] is completely stored in mice, rats and humans; and in the sequence DHDPS_1(PROSITE AC.PS00665)[GSA]-[LIVM]-[LIVMFY]-x(2)-G-[ST]-[TG]-G-E-[GASN F]-x(6)-[EQ], 8 of 10 non-convertible amino acid residues are stored.

From the above, the novel 35 kda protein has a primary structure similar to that of the known DHDPS family protein, and it is presumed that the novel protein may be a protein of the DHDPS family and may have a function of class I aldolase activity.

Enzyme that participates in sugar metabolisms universally exists from microorganisms to mammals, but regarding the 35 kd protein, its homologous gene was found only in mammals such as humans and rodents.

In addition, its gene expression is limited to livers, kidneys and testes. Accordingly, it is considered that the 35 kd protein participates in the metabolic route added especially to the livers and kidneys of mammal for some purposes, in addition to the sugar metabolic system universally existing in animals.

In higher animals, it is believed that the glycolytic system and the gluconeogenic system may be in a relationship of reciprocal reaction that is catalyzed by a common enzyme except some rate limiting enzymes. Especially in mammals, the glucose production (gluconeogenesis) has evolved in the livers and the kidneys as an indispensable function for ensuring the existence of individuals over starvation.

However, for men of today, the promotion of liver sugar production is a characteristic of the symptom of diabetes. It has heretofore been considered that the promotion of sugar production will be a change in the balance of the glycolytic system and the gluconeogenic system. Specifically, it has been believed that the promotion of sugar production will be because the level of the gluconeogenic system may be higher than that of the glycolytic system.

It has been considered that, since the substance WF00144 that specifically binds to the 35 kd protein may inhibit liver sugar production and has hypoglycemic effect in disease model animals, the 35 kd protein may exhibit its function in a sugar production route that differs from the sugar decomposition/sugar production system heretofore known in the art. Specifically, it is presumed that, in livers and kidneys, the 35 kd protein may exist in a route which has evolved for efficiently producing glucose separately from the glycolytic system therein.

Accordingly, the 35 kd protein and the novel sugar metabolic system that contains it are useful targets for development of novel medicines for diabetes.

Concretely, the invention is described below.

[1] A polynucleotide of any of the following (a) to (e), encoding a protein that specifically binds to a substance WF00144:

(a) a polynucleotide containing a base sequence of SEQ ID NO: 1 or 3;

(b) a polynucleotide encoding a protein that comprises an amino acid sequence of SEQ ID NO: 2 or 4;

(c) a polynucleotide encoding a protein that comprises an amino acid sequence of SEQ ID NO: 2 or 4 where one or plural amino acids are substituted, deleted, inserted and/or added;

(d) a polynucleotide hybridizing with a polynucleotide that comprises a base sequence of SEQ ID NO: 1 or 3, under a stringent condition;

(e) a polynucleotide having at least (1) 88% homology, (2) 92% homology or (3) 96% homology to the base sequence of SEQ ID NO: 1 or 3.

[2] A polynucleotide encoding a partial peptide of the protein encoded by the polynucleotide of [1].

[3] A peptide or protein encoded by the polynucleotide of [1] or [2].

[4] A vector containing the polynucleotide of [1] or [2].

[5] A transformant having the polynucleotide of [1] or [2], or a vector having the polynucleotide of [1] or [2].

[6] A method for producing the peptide or protein of [3], which includes a step of cultivating the transformant of [5] and collecting the expressed product.

[7] A polynucleotide comprising a base sequence complementary to the polynucleotide of [1] or [2] or to the complementary chain thereof, and having a length of at least 15 bases.

[8] An antibody to the peptide or protein of [3].

[9] An immunoassay method including a step of observing the immunological reaction between the peptide or protein of [3] and an antibody to the peptide or protein of [3].

[10] A screening method for a sugar production-regulating substance, which includes the following steps:

(1) a step of contacting a candidate substance with cells that express a protein encoded by the polynucleotide of [1]; and (2) a step of cultivating the cells under the condition under which the synthesis of the protein encoded by [1] is induced, and selected the candidate substance that regulates sugar production.

[11] A screening method for a sugar production-regulating substance, which includes the following steps:

(1) a step of contacting a candidate substance with cells having a vector introduced thereinto, where the vector contains a region of regulating the expression of a gene that comprises the base sequence of SEQ ID NO: 1 or 3 and a reporter gene functionally bound downstream to the region;

(2) a step of measuring the activity of the reporter gene; and (3) a step of selecting the candidate substance that increases or decreases the reporter activity in the step (2), as compared with a control.

[12] A medicine that contains the compound obtained according to the method of [10] or [11].

[13] A medicine that contains the peptide or protein of [3].

[14] A medicine that contains an anti-sense polynucleotide to the protein-encoding sequence of the polynucleotide of [1].

[15] A medicine of [12] or [13], which is for prevention or treatment of diabetes.

[16] Use of the compound obtainable according to the method of [10] or [11], for regulation of sugar production.

[17] A method of detecting diabetes, which includes the following steps:

(1) a step of determining the expression condition of the polynucleotide of [1];

(2) a step of comparing the determined result in (1) with the polynucleotide expression condition in a normal state;

(3) a step of correlating the change in the polynucleotide expression condition with diabetes, as a result of the comparison.

[18] A polynucleotide of encoding a protein, which comprises an amino acid sequence of SEQ ID NO: 2 or 4 where one or a few amino acids are substituted, deleted, inserted and/or added, and which has a dominant-negative phenotype to the protein that comprises the amino acid sequence of SEQ ID NO: 2 or 4.

[19] A screening method for a sugar production-regulating substance, which includes the following steps:

(1) a step of contacting a candidate substance with the peptide or protein encoded by [1];

(2) a step of determining the binding condition of the peptide or protein to the candidate substance, and selecting the complex;

(3) a step of separating the candidate substance from the complex selected in the previous step.

The protein that participates in sugar production of the invention and the polynucleotide that encodes the protein have all or a part of the sequence of any of SEQ ID NO: 1 to 4.

The polynucleotide of the invention is not specifically defined in point of its morphology so far as it encodes the protein of the invention, and it includes genome DNAs and chemically-synthesized DNAs in addition to cDNAs. So far as it encodes the protein of the invention, the polynucleotide includes any ones having any base sequence based on polycondensation of genetic codes.

As in the above, the polynucleotide that encodes the protein of the invention may be isolated in any ordinary method of, for example, hybridization with a probe of the polynucleotide sequence of SEQ ID NO: 1 or 3 or a part of it, or PCR with a primer designed on the basis of the information of such polynucleotide sequence.

The protein of the invention that participates in sugar production may be obtained, for example, by expressing it in a transformant that is prepared through transformation with an expression vector containing an open reading frame sequence of SEQ ID NO: 1 or 3.

The expressed protein may be purified and isolated from cell fractions in any ordinary method. Concretely, the purification and isolation method is as follows: First, the cells are collected in any ordinary manner of filtration, centrifugation or the like, and the cell walls and/or the cell membranes of the cells are processed in an ordinary manner to obtain a cytoplasm fraction.

Next, the cytoplasm fraction is dissolved in a suitable aqueous solution. Then, the protein of the invention is isolated and purified from the cytoplasm fraction according to an ordinary method generally employed for purification and isolation of natural or synthetic proteins. Examples of the isolation and purification method are dialysis, gel filtration, affinity column chromatography with a monoclonal antibody to the protein of the invention or to the partial peptide thereof, column chromatography on a suitable adsorbent, high-performance liquid chromatography, etc.

The invention encompasses a polynucleotide that encodes a protein functionally equivalent to the above-mentioned protein. The wording "functionally equivalent" as used herein means that the intended proteins are materially the same in point of their function in living bodies. Specifically, anyone skilled in the art may prepare the protein that is functionally equivalent to the novel 35 kd protein of the Example of the invention, for example, by utilizing a method of introducing mutation into the amino acid sequence of protein (for example, a site-specific mutagenesis (*Current Protocols in Molecular Biology*, edit. Ausubel et al., (1987) publish. John Wily and Sons, Sections 8.1-8.5)).

The protein of the type may be formed through mutation of amino acids in the natural world. So far as they have the equivalent function as that of the protein identified in the Example of the invention, any other proteins having the amino acid sequence of the identified protein (amino acid sequence of the protein encoded by SEQ ID NO: 2 or 4) in which, however, one or plural amino acids are substituted, deleted, inserted and/or added are within the scope of the present invention.

The plural amino acids as referred to herein are not specifically defined in point of the mutation number of the amino acids and the mutation sites thereof in the protein, so far as the protein keeps its function. The mutation number is typically within 10% of all amino acids, preferably within 5% of all amino acids, more preferably within 1% of all amino acids. As the case may be, the invention may encompass a protein with mutation of a few amino acids as plural amino acids. The wording "a few" as used herein means, for example, 5, or 4 or 3, or 2 amino acids, or even one amino acid.

Preferably, the amino acid to be substituted for an original one has properties similar to those of the original amino acid. For example, Ala, Val, Leu, Ile, Pro, Met, Phe and Trp are all within a group of non-polar amino acids, and they may have similar properties. Non-chargeable amino acid includes Gly, Ser, Thr, Cys, Tyr, Asn and Gln. Acidic amino acid includes Asp and Glu. Basic amino acid includes Lys, Arg and His.

The protein that is functionally equivalent to the 35 kd protein of the Example of the invention may be isolated by utilizing hybridization technology or gene amplification technology well known to those skilled in the art. Specifically, anyone skilled in the art may generally isolate a polynucleotide that has a high homology to the polynucleotide encoding the protein identified in the Example of the invention, on the basis of the base sequence (SEQ ID NO: 1 or 3) of the polynucleotide that encodes the identified protein or on the basis of a part of the base sequence and by the use of a hybridization technique (*Current Protocols in Molecular Biology*, edit. Ausubel et al., (1987), publish. John Wily and Sons, Sections 6.3-6.4), and may obtain a protein functionally equivalent to the identified protein, from the isolated polynucleotide.

So far as they have a function equivalent to that of the protein identified in the Example of the invention, other proteins encoded by a polynucleotide capable of hybridizing with the polynucleotide that encodes these proteins are within the scope of the invention. The stringent condition for hybridization for isolating the polynucleotide that encodes the protein functionally equivalent to the identified protein is generally "1×SSC, 0.1%, SDS, 37° C." or so for washing; a more stringent condition for it is "0.5×SSC, 0.1%, SDS, 42° C." or so; an even more stringent condition for it is "0.1× SSC, 0.1%, SDS, 65° C." or so. Under such a more stringent hybridization condition, isolation of a polynucleotide having a high homology to the probe sequence may be expected.

However, the combinations of SSC, SDS and temperature mentioned above are to indicate only some examples, and anyone skilled in the art could readily realize any other stringent conditions like the above by suitably combining the above-mentioned and other factors for determining the hybridization stringency (e.g., probe concentration, probe length, hybridization reaction time).

The protein thus isolated by the use of the hybridization technique as above generally have a high homology in point of the amino acid sequence thereof or of the base sequence to encode the protein, as compared with the protein encoded by SEQ ID NO: 2 or 4. The high homology is meant to indicate the sequence homology of at least 80%, preferably at least 84%, more preferably at least 88%, even more preferably at least 92%, most preferably at least 96%.

The homology may be determined by the use of BLAST2 retrieval algorism (Altschul, S. F. et al., 1997, Gapped BLAST and PSI-BLAST: a new generation of protein database search programs, *Nucleic Acid Res.* 25, pp. 3389-3402).

Another method is possible, which is as follows: According to a gene amplification technique (PCR) (*Current Protocols in Molecular Biology*, edit. Ausubel et al., (1987), publish. John Wiley and Sons, Sections 6.1-6.4), a primer is designed on the basis of a part of the polynucleotide sequence (SEQ ID NO: 1 or 3) identified in the Example of the invention, and polynucleotide fragments having a high homology to the polynucleotide sequence or to a part thereof are isolated, and based on these, a protein functionally equivalent to the protein identified in the Example of the invention is obtained.

The invention also relates to a partial peptide of the protein of the invention, and to a polypeptide of encoding the partial peptide. The partial peptide of the invention comprises an amino acid sequence of at least 7 amino acids, preferably at least 9 amino acids, more preferably at least 12 amino acids, even more preferably at least 15 amino acids. The partial peptide of the invention may be produced, for example, according to a gene engineering method or a known peptide synthesis method, or by cleaving the protein of the invention with a suitable peptidase.

The invention also provides an expression vector that contains any of the above-mentioned polynucleotides. Further, the invention relates to a transformant that carries the above-mentioned polynucleotide or any vector mentioned above, and to a method for producing a protein participating in sugar production or a partial peptide thereof, by cultivating the transformant and isolating the protein of the invention from the culture. Further, the invention provides the protein produced according to the method as above, or a partial peptide thereof.

When a polypeptide is produced according to a gene recombination method, it is well known to those skilled in the art that various polypeptides that differ in point of the type and the degree of glycosylation thereof are obtained depending on the type of the host cells used, and that the terminal (N-terminal and/or C-terminal) amino acid sequence of the precursor polypeptide expressed in the host cells is processed with a signal peptidase or the like and therefore various polypeptides having a different terminal amino acid sequence are obtained. Accordingly, anyone skilled in the art could easily understand that such polypeptides are naturally within the scope of the protein of the invention.

The following Example illustrates construction of an expression vector that functions in prokaryotes, especially in *E. coli*. However, as a result of disclosure of the polynucleotide that encodes the protein of the invention, it is easy for anyone skilled in the art to construct, on the basis of it, an expression vector which, when introduced into host cells of fungi such as yeast or into those of mammals, may make the hosts express and produce the protein of the invention. Accordingly, the invention encompasses the expression vector that is constructed according to the methods well known in the art on the basis of the polynucleotide sequence of the invention.

Microorganismic cells capable of being used for expression of the polynucleotide of encoding the protein of the invention include, for example, prokaryotic bacteria (*Escherichia coli, Bacillus subtilis*) and eukaryotic yeast (e.g., *Saccharomyces cerevisiae*). The mammal cells include cultivated human cells and cultivated animal cells. In addition, cultivated plant cells are also usable herein.

For facilitating the purification thereof, a basic amino acid having an affinity to metal ion chelates may be added to any terminal of the protein of the invention.

Such a basic amino acid may be added as follows: Using a primer with a series of base sequences of encoding desired amino acids added to the 5'-side thereof, PCR is carried out, whereby a desired oligopeptide may be added to any desired terminal of the intended gene. The basic amino acid includes histidine, lysine, arginine.

The polynucleotide encoding the amino acid sequence of the protein of the invention may be obtained through partial synthesis or complete synthesis, for example, by the use of an DNA synthesizer. Apart from this, it may also be obtained by the use of a probe or primer designed on the basis of the base sequence of SEQ ID NO: 1 or 2 from a human cDNA library.

Further, a genome DNA that encodes the protein of the invention may be prepared by processing a genome DNA in an ordinary manner (for example, by digestion with restriction enzyme, dephosphorylation with bacterial alkali phosphatase, phosphorylation with T4 polynucleotide kinase, ligation with T4 DNA ligase). In addition, utilizing the thus-obtained genome DNA, the transcription initiation point in the gene of the invention in the genome may be clarified, and the expression control region existing upstream the point may be specifically identified.

The control region such as promoter and enhancer of controlling the expression of the gene that encodes the protein of the invention is useful as a target region for detecting any expression failure in producing the protein of the invention. Further, expression control may be realized in decoy nucleic acid medicines that target the region.

The host cells for use in the invention include cells that are used for analysis of the function of the protein of the invention and those for screening function inhibitors and function promoters by utilizing the protein. The vector introduction into host cells may be attained, for example, according to a calcium phosphate precipitation method, an electric pulse perforation method (*Current Protocols in Molecular Biology*, edit. Ausubel et al., (1987), publish. John Wiley and Sons, Sections 9.1-9.9), a lipofectamin method, or a microinjection method. Preparation of the protein of the invention from transformant may be attained through protein isolation and purification well known to those skilled in the art.

The invention also provides a polynucleotide comprising a base sequence complementary to the polynucleotide of the base sequence of SEQ ID NO: 1 or 3 or to the complementary chain thereof, and containing at least 15 nucleotides.

The "complementary chain" as referred to herein indicates the other chain opposite to one chain of a double-stranded polynucleotide that comprises a base pair of A:T (A:U), G:C. The term "complementary" is not limited to the case where the region of at least 15 continuous nucleotides has a completely complementary sequence, but includes any others having at least 70%, preferably at least 80%, more preferably at least 90%, even more preferably at least 95% homology in point of the base sequence of the region. The algorism to determine the homology is described herein.

The polynucleotide of the type may be utilized as a probe for detecting and isolating DNA and RNA that encode the protein of the invention, or as a primer for amplifying the polynucleotide of the invention.

When it is used as a primer, in general, it has a chain length of from 15 bp to 100 bp, preferably from 15 bp to 35 bp. When used as a probe, the polynucleotide has at least a part or all of the sequence of the polynucleotide of the invention and has a chain length of at least 15 bp. When used as a primer, the 3'-side region of the polynucleotide must be complementary, but the 5'-side thereof may have a restriction enzyme recognition site or a tag added thereto.

The polynucleotide of the invention may be utilized for medical examination and diagnosis of abnormality of the protein of the invention. For example, in northern hybridization or RT-PCR where the polynucleotide of the invention is used as a probe or primer, the protein expression failure may be detected.

The term "expression" as used herein includes transcription and/or translation. The expression analysis by the use of the polynucleotide of the invention makes it possible to examine and diagnose gene expression on the gene transcription level.

When the antibody to the protein of the invention, which is described hereinunder, is used, then gene expression may be examined and diagnosed on the gene translation level. In addition, the polynucleotide that encodes the protein of the invention or its expression control region may be amplified through genome DNA-PCR or RT-PCR in which the polynucleotide of the invention is used as the primer in the polymerase chain reaction (PCR), and the sequence disorder may be examined and diagnosed through RFLP analysis, SSCP, sequencing or the like method.

The "polynucleotide complementary to the polynucleotide of the base sequence of SEQ ID NO: 1 or 2 or to the complementary chain thereof, and containing at least 15 nucleotides" includes anti-sense polynucleotide that inhibits the expression of the protein of the invention. The anti-sense polynucleotide causes an anti-sense effect, and therefore it has a chain length of at least 15 bp, preferably at least 100 bp, more preferably at least 500 bp, but generally at most 3000 bp, preferably at most 2000 bp.

The anti-sense polynucleotide of the type may be applied to gene therapy for diseases caused by abnormality (functional abnormality or expressional abnormality) of the protein of the invention. Concretely, for diabetes, the anti-sense polynucleotide may be prepared, for example, according to a phosphorothioate method (Stein, 1988, Physicochemical Properties of Phosphorothioate Oligodeoxynucleotides, *Nucleic Acids Res.* 16, pp. 3209-3221 (1988)), based on the sequence information of the polynucleotide of SEQ ID NO: 1 or 3.

When the polynucleotide or the anti-sense polynucleotide of the invention is used in gene therapy, then it is administered to patients according to an ex-vivo method or an in-vivo method using, for example, a viral vector such as retrovirus vector, adenovirus vector, adeno-associated virus vector, or a non-viral vector such as liposome.

The invention also provides an antibody that binds to the protein of the invention. The antibody of the invention is not specifically defined in point of its morphology, and includes a polyclonal antibody, a monoclonal antibody and a part of them having the ability to bind with antigen. It further includes antibodies of all classes. In addition, the antibody of the invention includes special antibodies such as humanized antibodies.

When the antibody of the invention is a polyclonal antibody, it may be obtained by immunizing rabbits with the protein or partial peptide of the invention produced herein (*Current Protocols in Molecular Biology*, edit. Ausubel et al., (1987), publish. John Wiley and Sons, Sections 11.12-11.13). On the other hand, when it is a monoclonal antibody, it may be obtained by immunizing mice with the protein or partial peptide of the invention, then hybridizing the spleen cells of the immunized mice with myeloma cells in a mode of cell fusion, and isolating the monoclonal antibody from the resulting hybridoma cells (*Current Protocols in Molecular Biology*, edit. Ausubel et al., (1987), publish. John Wiley and Sons, Sections 11.4-11.11).

The antibody that binds with the protein of the invention maybe utilized for purification of the protein of the invention and, for example, additionally for medical examination and diagnosis of expression abnormality or structure abnormality of the protein. Concretely, for example, protein is extracted from tissue, blood or cells, and this is subjected western blotting, immunoprecipitation, ELISA or the like to detect therein the protein of the invention whereupon the presence or absence of the expression or structure abnormality of the protein may be examined and diagnosed.

The antibody that binds with the protein of the invention may be utilized for the purpose of treatment of diseases associated with the protein of the invention. When the antibody is used for the purpose of treatment of patients, then it is preferably a human antibody or humanized antibody as its immunogenicity is low. The human antibody may be prepared by immunizing mice of which the immune system has been changed to a human immune system (for example, Functional Transplant of Megabase Human Immunoglobulin Loci Recapitulates Human Antibody Response in Mice, Mendez, M. J. et al., (1997) *Nat. Genet.* 15, pp. 146-156). On the other hand, the humanized antibody may be prepared through genetic recombination with an ultravariable region of a monoclonal antibody (*Methods in Enzymology* 203, pp. 99-121 (1991)).

The protein of the invention that is encoded by the polynucleotide of SEQ ID NO: 2 or 4 participates in the regulation of sugar production, as so mentioned hereinabove in relation to the regulation of sugar production. Accordingly, when the expression of the protein of the type is enhanced, then it retards sugar production and is therefore effective for treatment and prevention of diabetes. Further, the protein of the type and the protein that is functionally equivalent to it may be used by themselves as a medicine for treatment and prevention of diabetes.

The invention also provides a screening method for a compound having the ability to regulate the activity of the protein of the invention. Since the protein of the invention participates in sugar production, the compound having the ability to regulate the expression of the product of the gene of the protein may regulate sugar production and is therefore useful as a medicine for treatment and prevention of diabetes. The screening method is described below.

The expression of the protein of the invention that is encoded by the polynucleotide of SEQ ID NO: 1 or 3 may be increased so as to retard sugar production, and it is effective for treatment and prevention of diabetes. Specifically, the invention relates to a screening method for a compound of regulating the expression of the protein encoded by the polynucleotide of the invention, and the method includes the following steps:

(1) a step of contacting a candidate substance with cells having a vector introduced thereinto, where the vector contains a region of regulating the expression of a gene that comprises the base sequence of SEQ ID NO: 1 or 3 and a reporter gene functionally bound downstream to the region;

(2) a step of measuring the activity of the reporter gene; and (3) a step of selecting the candidate substance that increases or decreases the reporter activity in the step (2), as compared with a control.

For the screening method of the invention, the control region of the gene is cloned from a chromosomal DNA, and a reporter gene (e.g., luciferase, β-galactosidase, GFP (green fluorescent protein)) is bound downstream to the control region of the gene to thereby construct an expression plasmid. The expression control region of the gene that comprises the base sequence of SEQ ID NO: 1 or 3 may be cloned from a chromosomal DNA in any known manner.

For example, an S1 mapping method is known for a method of identification of a transcription initiation point ("Isolation of Transcription Control Region" and "Identification and Purification of Transcription Control Factor", *Cell Engineering*, extra. ed. 8, New Cell Engineering Experience Protocols, edit. Tokyo University, Medical Science Laboratory, Carcinostatic Laboratory Section, publish. Shujun-sha, 1993, pp. 362-374).

In general, the expression control region DNA of the gene is cloned as a gene clone that contains the expression control region, by screening a human genomic library with a segment of from 15 to 100 bp, preferably from 30 to 50 bp of the 5'-terminal of the gene that serves as a probe DNA.

Thus obtained, the clone often contains a 5'-non-translation region of the gene having a length of at least 10 kbp. Accordingly, the 5'-terminal of the clone is shortened or fragmented through exonuclease treatment or the like. Using the sequence thus containing the shortened expression control region, the expression intensity and the expression regulation of the reporter gene is determined, and it gives the minimal indispensable unit for maintaining the activity of the expression control region (deletion study).

In addition, a program of forecasting the expression control region of gene by the use of Neural Network is known ([[http://]]www.fruitfly.org/seq_tools/promoter.html, Reese, M. G. et al., "Large Scale Sequencing Specific Neutral Networks for Promoter and Splice Site Recognition" Biocomputing: Proceedings of the 1996 Pacific Symposium, edited by Lawrence Hunter and Terri E. Klein, World Scientific Publishing Co., Singapore, Jan. 2-7, 1996). It is also possible to forecast the minimal unit of activity by the use of a program for forecasting the expression control region through retrieval of transcription factor binding sequences such as Promoter Scan ([[http://]]biosci.cbs.umn-.edu/software/proscan/promoterscan.htm, Prestridge, D. S. 1995, Prediction of Pol II Promoter Sequence Using Transcription Factor Binding Site, *J. Mol. Biol.*, 249, pp. 923-932). Further, deletion study may also be carried out around the center of the forecasted core part.

A reporter gene is functionally bound downstream to the thus-isolated control region of the gene to construct an expression plasmid, and this expression plasmid is introduced into suitable cells.

In the invention, functional binding means that the two are bound to each other in such a manner that the transcription of the reporter gene could be initiated by the activation of the expression control region.

For the reporter gene, any one can be utilized so far as it encodes a protein in which the activation of the expression control region can be observed as the expression of the gene. Concretely, for example, a gene such as luciferase, β-galactosidase, GFP (green fluorescent protein) may be generally used as the reporter gene.

For the cells into which the vector is introduced, for example, usable are animal cells where the gene is deleted. Next, for example, the animal cells where the gene is deleted are transformed with the expression plasmid. The expression of the reporter gene owing to the control region transcription activity in the cells is detected as color formation or light emission.

Under the condition as above, the cells are sown in a 96-well multi-plate, and the compound to be screened is added to each well. In this, accordingly, it is possible to easily select the compound capable of inhibiting or promoting the expression of the expression product of the gene.

The method of selecting the compound is described. For example, when GFP is used for the reporter gene, then the quantity of light emission by GFP in the case where the chemical is added is compared with that in the other case where the chemical is not added, and it is possible to select the compound. The comparison indicates a light emission quantity ratio of at least 2 times or at most ½ times, preferably at least 5 times or at most ⅕ times, more preferably at least 10 times or at most ¹⁄₁₀ times. In the method, usable are not only animal cells but also any other hosts, irrespective of eukaryotes or prokaryotes, capable of inducing reporter gene expression in the same system.

The sample to be tested in the screening method includes, for example, cell extracts, gene library expression products, low-molecular synthetic compounds, synthetic peptides, natural compounds. The test samples described herein are only examples, to which, therefore, the invention should not be limited.

The compounds isolated through the screening method are candidates for the compounds that promote or inhibit the activity of the protein of the invention (agonists, antagonists).

In addition, they are candidates for the compounds that inhibit the interaction between the protein of the invention and a molecule capable of interacting with the protein. These compounds may be applicable to medicines for prevention or treatment of diseases associated with the protein of the invention.

In addition, the invention relates to the medical use of the compounds that are obtained according to the screening method of the invention. Specifically, the invention relates to a medicine that contains the compound obtained according to the screening method and to a pharmaceutical composition that contains the compound as the principal ingredient thereof.

The protein, the nucleotide, the antibody and the compound isolated through the screening of the invention are useful for regulation of sugar production and for medicines for diabetes.

When these are used for medicines, they may be directly used as medicines by themselves, but may be formulated into pharmaceutical composition according to known pharmaceutical formulation methods. For example, they may be combined with pharmaceutically-acceptable carriers or mediums, concretely sterile water, physiological saline, vegetable oil, emulsifier, suspending agent or the like, to be formulated into pharmaceutical compositions.

The administration of the medicines to patients may be effected in any method known to those skilled in the art, for example, through intra-arterial injection, intravenous injection, subcutaneous injection, etc. The dose may vary, depending on the body weight and the age of patients, and on the administration route. Anyone skilled in the art could readily determine the suitable dose.

When the compound can be encoded by a polynucleotide, then the polynucleotide may be inserted into a vector for gene therapy, and it may be used for gene therapy.

The dose and the administration route may vary, depending on the body weight, the age and the condition of patients, and anyone skilled in the art could readily determine the suitable dose.

It is possible to know as to whether or not the protein of the invention may be associated with any other disease, by using an antibody specifically recognizing the protein of the invention, apart from those mentioned hereinabove, and determining the correlation between the specific disease and the expression quantity and the activity of the protein.

In addition, the protein of the invention may be analyzed with reference to "Molecular Diagnosis of Genetic Diseases" (edit. Rob Elles, 1996) in a series of *Method in Molecular Biology* (publish. Humana Press).

The antibody that binds to the protein of the invention may be utilized for medical examination and diagnosis of expression abnormality or structure abnormality of the protein of the invention, in addition to the use for purification of the protein of the invention.

Concretely, for example, protein is extracted from tissue, blood or cells, and this is subjected western blotting, immunoprecipitation, ELISA or the like to detect therein the protein of the invention whereupon the presence or absence of the expression or structure abnormality of the protein may be examined and diagnosed.

Further, it is possible to detect diabetes by determining the expression condition of the polynucleotide of the invention.

Accordingly, the invention relates to a method for detecting diabetes that includes the following steps:
(1) a step of determining the expression condition of the polynucleotide having at least one sequence selected from a group of SEQ ID NO: 1 and SEQ ID NO: 2,
(2) a step of comparing the determined result in (1) with the polynucleotide expression condition in a normal state;
(3) a step of correlating the change in the polynucleotide expression condition with diabetes, as a result of the comparison.

In the invention, the expression condition of the polynucleotide may be clarified by analyzing any one stage in the process where the gene is transcribed to mRNA and is translated into protein. More concretely, for example, the transcription condition may be known by measuring the mRNA that comprises the above-mentioned base sequence as the above-mentioned polynucleotide. The mRNA may be determined in any known method of northern hybridization or RT-PCR.

In addition, when the protein that comprises the amino acid sequence encoded by the above-mentioned polynucleotide or its fragment is analyzed, then the translation condition into the protein can be known. The protein can be determined through western blotting with an antibody that recognizes it or through various immunoassay.

The examination method of the invention may be carried out with objects of patients' blood samples or cerebrospinal fluid samples. For observing the expression condition of the polynucleotide of the invention in a sample of tissue specimens, employable is in-situ hybridization or tissue immunoassay. When the expression condition of the polynucleotide of the invention in the sample is analyzed and when the polynucleotide expression therein is retarded as compared with that in a control case with no abnormality in sugar production regulation, then the sample may be associated with diabetes.

The invention further relates to a reagent for clarifying the expression condition of the polynucleotide of the invention. More concretely, the invention relates to the use of a polynucleotide complementary to the polynucleotide of the invention or to the complementary chain thereof and having a length of at least 15 bases, for detection of the polynucleotide of the invention.

Further, the invention also relates to the use of an antibody that recognizes the protein of the invention, for detection of the protein.

BRIEF DESCRIPTION OF THE DRAWING

FIG. 1 is a structural formula of a substance WF00144.

BEST MODE FOR CARRYING OUT THE INVENTION

The invention is described more concretely with reference to the following Examples, to which, however, the invention should not be limited.

1. Identification of Rat and Human 35 kd Protein, and Acquisition of the Gene Thereof 1-1. Formation of Affinity Probe:

Biotin was bonded to the carboxylic acid part of a substance WF00144 (WO99/61645) in a mode of amidobonding via a spacer to form a biotin-modified substance WF00144 (hereinafter referred to as a biotinated substance WF). The biotinated WF substance had a sugar production inhibitory activity in primary liver cells.

1-2. Preparation of Sugar Production-Inducing Rat Primary Liver Cells, and Method for Determination of Sugar Concentration:

Rats (male, 200 to 250 g) with no feed given from the previous day were anesthetized and their abdomens were cut open out. An indwelling needle was inserted into the portal vein of each rat and fixed thereto, and, with a pre-perfusion liquid (8 g/liter sodium chloride, 0.4 g/liter potassium chloride, 0.078 g/liter $NaH_2PO_4.2H_2O$, 0.151 g/liter $Na_2HPO_4.12H_2O$, 2.38 g/liter HEPES, 0.006 g/liter phenol red, 0.19 g/liter EGTA, 0.35 g/liter sodium hydrogencarbonate, 0.9 g/liter glucose) introduced thereinto, the abdominal aorta was cut to bleed out, and the liver was perfused.

Next, the liver was perfused with a collagenase liquid (8 g/liter sodium chloride, 0.4 g/liter potassium chloride, 0.078 g/liter $NaH_2PO_4.2H_2O$, 0.151 g/liter $Na_2HPO_4.12H_2O$, 0.74 g/liter $CaCl_2$, 2.38 g/liter HEPES, 0.006 g/liter phenol red, 0.05 g/liter trypsin inhibitor, 0.35 g/liter sodium hydrogencarbonate, 0.4 g/liter collagenase (type III: Sigma)) to liberate the liver cells. The liver was cut off, its coating membrane was torn off, and the cells were dispersed in an MEM medium (minimum essential medium with Eargle's salts).

The dispersed cells filtered through gauze, and the filtrate was centrifuged. The supernatant was removed, an MEM medium was added to it, and the cells were again dispersed therein, and this was centrifuged in the same manner. This operation was repeated 5 times to prepare a liver cell suspension.

The cell suspension was transferred to a 10-cm dish coated with collagen, and incubated therein under a condition of 37° C., 5% $CO_2$, 30% $O_2$ and 100% humidity, for 6 hours, and the liver cells were adhered to the dish.

The medium was changed to a Dulbecco's MEM medium (-glucose, 1% FBS, 83 mg/liter streptomycin, 83 mg/liter penicillin, 100 mg/liter kanamycin, 20 mM pyruvic acid, 0.01 mM glucagon, pH 7.2), in which the liver cells were incubated for one full day so as to make them induce sugar production.

The concentration of glucose produced in the cell culture was quantified with Glucose Test Wako (Wako Pure Chemical's glucose metering kit) according to its manual.

1-3. Preparation of Sugar Production-Inducing Primary Liver Cell Extract:

The rat primary liver cells in which sugar production had been induced overnight were collected from the dish, and then washed once with a phosphate buffered physiological saline (PBS), and the weight of the liver cell pellets was measured.

The cell pellets were suspended in a cell extraction solution (0.25 M sucrose-aqueous solution) of 9 times the weight thereof, and ultrasonically disrupted. The cell debris was removed through low-speed centrifugation, and the supernatant was super-centrifuged (100,000 g, 30 minutes). The residue was removed, and a sugar production-inducing primary liver cell extract was thus obtained.

1-4. Biotin/Avidin Affinity Chromatography:

Biotin/avidin affinity chromatography was carried out in an ordinary manner (*FEBS Lett.,* 31, 149, (1973)).

Precisely, 10 mM biotinated WF was added to the liver cell extract obtained in the previous step, and reacted with it overnight at 4° C. At the same time, a control group was prepared, in which WF00144 (100 mM) was added to the cell extract along with the biotinated WF thereto so as to make the two antagonize to each other.

The reaction solution was dialyzed overnight to the cell extract solution to remove the unbinding biotinated WF. An avidin-bound resin (from Pierce) was added to the reaction solution and reacted with it overnight.

The avidin-bound resin was precipitated through centrifugation, and the supernatant was removed. Then, the resin was washed three times with a washing solution (0.5 M salt-added cell extract). Avidin on the resin was degenerated with 8 M urea, and the bound protein was eluted out.

The eluted protein was separated through electrophoresis with SDS polyacrylamide gel (12%). The gel was stained with CBB, and the protein bands were observed. Of the protein bands thus observed, those not observed in the separately-prepared, avidin-bound resin alone group (biotinated WF not added thereto) and in the WF00144-added group are specific binding protein bands.

1-5. Identification of Rat 35 kd Protein:

The band of the specific binding protein observed at around a molecular weight of 35 kd was cut out of the gel, and subjected to in-gel trypsin digestion to form peptide fragments. The molecular weight of each peptide fragment was determined according to a peptide mass finger method (MALDI-TOFMS) (using Tofspec 2E from Micromass), and the data were retrieved from the database. As a result, a peptide fragment anticipated from the base sequence of rat EST clone (gi: 8504516), GRMNSAALIHHYTKVADL-SPIPVVLYSVPGNTGLELPVDAV-VTLSQHPNIIGLKDSGGD VTR TGLIVHKTSKQDFQVLAGSVGFLLASYAVGAVGGIC GLANVLGAQVCQLERLCLTGQGEAAQRLQHR LIEPNTAVTRRFGIPGLKKTMDWFGYYGGPCRAPLX ELSPSEEEALRL DFSNNGWL QAGDTWSELSQTLVPTV was identified.

Of the fragment, the underlined amino acid sequences were determined from the peptides that had been actually prepared from the 35 kd bands, according to a peptide sequence-tag method (ESI-TOF MS/MS) (using Q-Tof-2 from Micromass).

Based on these data, Riken mouse clones were analyzed, and it was considered that a Riken mouse clone 060010D20 would be a homologous protein to the rat 35 kd protein.

1-6. Acquisition of Rat and Human 35 kd Protein Gene:

A rat cDNA library was prepared with Gibco BRL's SuperScript Choice System, using the total RNA prepared from the above-mentioned, sugar production-inducing rat primary liver cells. A human cDNA library was bought from Clontech.

Based on the base sequence information of the EST clone to the partial amino acid sequence of the present protein that had been determined previously, an oligonucleotide primer was designed for obtaining the gene corresponding to about a half at the C-terminal thereof (SEQ ID NO: 7).

In addition, from the base sequence information of Riken clone 0610010D20, an oligonucleotide primer was designed for obtaining the gene corresponding to about a half at the N-terminal thereof (SEQ ID NO: 6).

From the thus-designed primers and the cDNA library that had been prepared from the above-mentioned rat sugar production-inducing primary liver cells, a complete-length gene was obtained according to a PCR method.

Based on the rat base sequence, primers (SEQ ID NO:s 8 and 9) were designed, and a human 35 kd-homologous gene was obtained from the human liver cDNA library according to a PCR method.

1-7. Sequence of Rat and Human 35 kd Protein Gene:

The DNA fragments of rat and human 35 kd protein for their sequencing were prepared by the use of Applied Biosystems' BigDye™ Terminator Cycle Sequencing Ready Reaction with AmpliTaq DNA Polymerase. The sequencing was carried out with Applied Biosystems' 3100 Genetic Analyzer.

Thus sequenced, the nucleotide sequence of the rat 35 kd protein and the amino acid sequence thereof are SEQ ID NO:s 3 and 4, respectively. The nucleotide sequence of the human 35 kd protein and the amino acid sequence thereof are SEQ ID NO:s 1 and 2, respectively.

As a result, the amino acid sequence-level homology between human and rat 35 kd proteins was 87%.

The amino acid-level homology between the Riken clone-encoding protein and the rat 35 kd protein and the human 35 kd protein was 96% and 88%, respectively.

2. Expression and Purification of Rat and Human 35 kd Protein 2-1. Construction of Expression Plasmid:

Invitrogen's pTrcHis B was used as an expression vector. The genes obtained in Embodiment 1-6 were cleaved with restriction endonucleases. Briefly, the rat gene was with BamHI and EcoRI; and the human gene was with BglII and EcoRI.

Each fragment was ligated with a fragment prepared by cleaving pTrcHis B with the same combination of restriction endonucleases to prepare a expression plasmid of 35 kd protein which a histidine tag-encoding sequence was bound to (rat: pTrcHisB/r35k, human: pTrcHisB/h35k).

2-2. Expression:

*E. coli* (DH5α) transformed with human or rat 35 kd protein expression vector pTrcHisB/h35k were planted in 5 ml of an L-medium containing 50 μg/ml ampicillin (L-Amp), and incubated therein with shaking overnight at 37° C.

The resulting culture was transferred into 200 ml of L-Amp, and shaken at 37° C. for 3 hours, and then IPTG was added to it to have a final concentration of 1 mM, and this was further shaken for 6 hours. The cultured cells were collected through centrifugation (6000 rpm, 20 min, 4° C.), and frozen and stored at −20° C.

2-3. Purification:

The cells obtained in the previous step were suspended in 40 ml of 25 mM Tris-HCl (pH 8.0) containing 0.5 mg/ml lysozyme and 0.3 M sodium chloride, and left at room temperature for about 15 minutes.

Next, this was ultrasonicated (10 min) with cooling with ice, and centrifuged (10,000 rpm, 20 min, 4° C.) to obtain a supernatant. The supernatant was collected, and passed through an Ni-NTA column (Qiagen, bed volume 5 ml) that had been equilibrated with 25 mM Tris-HCl (pH 8.0) containing 0.3 M sodium chloride, and the column was washed with a 4-times amount of the same buffer and then with the same amount of the same buffer containing 20 mM imidazole. The intended protein was eluted with 10 ml of the same buffer containing 200 mM imidazole, and the eluate was collected and concentrated to about 6 ml by the use of a ultrafiltrational concentrator (ULTRAFREE, BIOMAX-10 k, Millipore).

The Ni-NTA purified fraction (6 ml) was dialyzed to 200 ml of 25 mM Tris-HCl (pH 8.0), and, for cutting and removing the His-tag from it, 5 μl of Tween 20, 50 μl of 100 mM CaCl$_2$ and 30 units of enterokinase (Invitrogen) were added to it and reacted at room temperature for about 8 hours.

After the cutting reaction, 5 mM DTT was added to the reaction liquid and left at room temperature for about 30 minutes. Then, this was subjected to ion-exchange chromatography with Mono Q 5/5 (Amersham Pharmacia).

Using 25 mM Tris-HCl (pH 8.0) as an equilibrated buffer, the column was subjected to linear gradient elution with a 20-columns volume of 0.5 M sodium chloride (flow rate 1 ml/min).

Based on the absorption at UV 280 nm, the intended protein fraction was collected and concentrated to about 0.8 ml through ultrafiltration (ULTRAFREE, BIOMAX-10, Millipore).

Next, this was subjected to gel filtration chromatography with Superdex 200HR 10/30 (flow rate; 0.5 ml/min, Amersham Pharmacia) equilibrated with 25 mM Tris-HCl (pH 8.0) containing 0.15 M sodium chloride, in which a single peak containing the intended protein was obtained.

Thus obtained, the sample was about 10 mg in protein assay (Bio-Rad), and it gave a single band at about 35 kda. in SDS-PAGE. analysis. From these results, it is understood that the rat and human 35 kd gene expressed in *E. coli* produced a protein having a suitable molecular weight presumed from the amino acid sequence thereof.

3. Specific Binding of Human 35 kd Protein to WF00144

Using the same biotinated WF as in the identification of the 35 kd protein and the human 35 kd protein expressed in *E. coli* and purified, the above-mentioned biotin/avidin chromatography was carried out, and the protein released from the avidin resin was analyzed through SDS-polyacrylamide gel electrophoresis to thereby investigate the specific binding of the human 35 kd protein to WF00144.

As a result, the purified human 35 kd protein was kept binding to the avidin resin only in the presence of the biotin-labeled substance. In addition, this binding was antagonized in the presence of WF00144 (in a molar ratio to the biotin-labeled substance of 1/1).

4. Determination of Molecular Weight Through Gel Filtration

According to the gel permeation chromatography with Superdex 200HR 10/30 that had been carried out in the step of purification, the molecular weight of the present protein was determined. Aldolase (MW: 158 kDa.), albumin (67 kDa.) and ovalbumin (43 kDa.) all from Amersham Pharmacia were used as molecular weight markers. The molecular weight of the 35 kda. protein that is calculated from the elution volume indicated by each marker was about 80 kDa.

From the molecular weight thereof (35 kda.) in the previous SDS-PAGE, it is considered that the present protein would have a dimer structure.

5. Tissue-Specific Expression of 35 kd Protein Gene

According to a process of PCR using Clonetech's Rat Multiple Tissue cDNA (MTC) panel I (cat. No. #K1429-1), the expression condition of the 35 kd protein gene in heart, brain, spleen, lung, liver, skeletal muscle and kidney was investigated. In PCR, a forward primer CTGTACAGTGTCCAGGCAACA and a reverse primer AATCCTGCTTGCTGGTCTTGTG were used, and the DNA polymerase was Toyobo's KOD-Plus. PCR was carried out according to the manual attached to the device. The PCR product was analyzed by separating the reaction liquid through ordinary agarose gel electrophoresis.

As a result, it is obvious that the expression of the 35 kd protein gene is limited to only liver and kidney. This result strongly suggests that the 35 kd protein gene is a protein that participates in sugar production.

In physiological function analysis of protein not known in point of its function, the specificity of the protein gene in tissue expression is useful. Sugar-producing organs are limited to liver and kidney. Accordingly, if the 35 kd protein participates in sugar production, then it is readily anticipated that the protein expression will be limited to only liver and kidney. Liver and kidney are organs that are highly differentiated in point of their function, and except sugar production, there is no other function common to such liver and kidney.

6. Certification of 35 kd Protein as Sugar Production-Associated Protein by the Use of Compound 6-1. Thinking of Function Certification by the Use of Compound:

WF00144 is a liver sugar production inhibitor that is produced by fungi, *Phoma* sp. No. 00144 (WO99/61645). This substance inhibits in-vitro sugar production by primary culture liver cells, and owing to its effect, this exhibits hypoglycemic effect in diabetes-diseased model animals.

Specifically, it may be said that this agent could be a medicine for diabetes, as binding to some protein that participates in liver sugar production and inhibiting it to thereby inhibit liver sugar production and express hypoglycemic effect. The 35 kd protein is a protein that specifically binds to the liver sugar production inhibitor WF00144, in the sugar production-inducing rat primary liver cells shown in Embodiment 1-2, or that is, in liver cells where their sugar-producing mechanism is active. Accordingly, it may be readily presumed that the 35 kd is a protein that participates in liver sugar production.

For finally analyzing the function of a novel protein, generally employed is a method of deleting, mutating or over-expressing the gene that encodes the protein so as to observe the phenotype of the gene on the level of cells or on the level of individuals. However, the genetic method of the type generally takes a long period of time, within which, however, some substitute mechanism may become active, and there will be many difficulties in accurate function analysis according to the method.

As a method of final function analysis of a novel protein capable of compensating for the drawbacks of the genetic method, we have herein employed a method of using a low-molecular compound, of which the reasonability has been established as Chemical genetics recently. The low-molecular compound may transitionally and reversibly inhibit a protein at any stage, or that is, at a stage at which the biological phenomenon that is to be observed has been induced (in general, this period is short), and may make it possible to observe the phenotype that is induced by it.

Accordingly, there should be no contradiction in thinking that, according to the method as above, "when a low-molecular compound, which specifically binds to a protein capable of specifically binding to a compound that inhibits and retards a certain pharmaceutical phenomenon and which differs from the latter compound in point of their molecular skeleton, may inhibit and retard the same pharmaceutical phenomenon as that of the latter compound, then the protein participates in the pharmaceutical phenomenon".

For example, in the present case, when some other low-molecular compound except the substance WF00144 that specifically binds to the 35 kd protein, of which the physiological function is not clear, may exhibit a rat liver sugar production-inhibiting activity like the substance WF00144, then it may be concluded that the present 35 kd protein participates in sugar production. Accordingly, low-molecular compounds capable of specifically binding to the 35 kd protein were searched for according to the method mentioned below, and compounds A and B were found out.

6-2. Selection of Compound and Determination of the Activity Thereof:

A solution containing the purified human or rat 35 kd protein obtained according to the same method as in the above-mentioned Embodiment 2 was mixed with a solution containing a test substance to form a protein-compound complex. The test substance, the protein and the mixture containing the protein-compound complex formed therein were separately analyzed with BiaCore S-51 (from BiaCore) to confirm the condition of the molecules and the complex. The analysis was carried out according to the operation manual of BiaCore S-51.

The data obtained through analysis with BiaCore S-51 confirmed that the test substance specifically bound to the protein. More concretely, the data of the kd binding value of the human 35 kd protein to the test substance measured with BiaCore S-51 are shown in Table 1.

Regarding the sugar production-inhibiting activity of the protein in rat primary liver cells, the data of IC50 thereof measured according to Embodiment 1-2 are shown in Table 1. From these results, it is presumed that the physiological function of the 35 kd protein would be liver sugar production.

TABLE 1

Sugar Production Inhibiting Activity of Compound Specifically Binding to Human 35 kd Protein

| Compound | 35 kd binding (Kd: µM) | Sugar Production Inhibiting Activity (IC$_{50}$: µM) |
|---|---|---|
| WF00144 | irreversible binding | 0.5 |
| Compound A | 91 | 27 |
| Compound B | 280 | 15 |

7. Confirmation of Aldolase Activity of Human 35 kd Protein, and Determination of the Enzyme Activity Thereof 7-1. Confirmation of Aldolase Activity:

According to the method described in Embodiment 2, expression and purification of rat and human 35 kd protein, the human 35 kd protein was prepared. The human 35 kd protein was suitably reacted with its substrate for enzymatic reaction, glycerylaldehyde 3-phosphate (GAP), dihydroxyacetone phosphate (DHAP) or fructose 1,6-bisphosphate (F1, 6P$_2$) in a reaction liquid having the following composition, at 37° C. for 30 minutes. Reaction liquid 100 µl: 0.25 mM tris-HCl buffer (pH 8.0), 0.5 mM glycerylaldehyde 3-phosphate (from Sigma), 0.5 mM dihydroxyacetone phosphate (from Sigma), human 35 kd protein (40 µg/ml).

The reaction mixture was subjected to TLC with a plate silica gel 60F$_{254}$ (from Merck), in which this was developed with a mixed solvent of butanol/acetic acid/water=4/1/2. After the development, the plate was dried and then the reaction product was analyzed through ordinary Molish reaction with α-naphthol and concentrated sulfuric acid.

The Rf value and the color formation of the three sugars in this analysis system are as follows: Glycerylaldehyde 3-phosphate (GAP), 0.28, brown; dihydroxyacetone phosphate (DHAP), 0.16, blue; fructose 1,6-bisphosphate (F$_1$, 6P$_2$) 0.05, reddish violet.

As a result, the human 35 kd protein formed fructose 1,6-bisphosphate from glycerylaldehyde 3-phosphate and dihydroxyacetone phosphate. In addition, the human 35 kd protein produced glycerylaldehyde 3-phosphate and dihydroxyacetone phosphate from fructose 1,6-bisphosphate. These reactions are aldol condensation reaction and aldol cleavage reaction, and are characteristic of Class I aldolase. Accordingly, it was confirmed that the human 35 kd protein is a type of Class I aldolase as so anticipated from its structure.

7-2. Determination of Aldolase Activity of Human 35 kd Protein:

The aldolase activity of the human 35 kd protein was determined as follows, according to the method described in a reference (*Novel Biochemistry Experiment Lectures*, Vol. 15, Metabolism Abnormality, p. 111, edit. Biochemical Society of Japan, publish. Tokyo Kagaku Dojin-sha, Sep. 22, 1992):

Conjugated with triose phosphate isomerase (TIM) and glycerol 3-phosphate dehydrogenase (G3PDH), the aldol cleavage reaction of fructose 1,6-bisphosphate (F1, 6P2) with the 35 kd protein was determined with NADH.

A reaction liquid having the composition mentioned below was prepared, and reacted at 37° C. for 30 minutes. The enzymatic reaction was monitored through the reduction in the 340 nm absorbance owing to the oxidation of NADH in the reaction liquid. The enzymatic reaction was indicated by the number of mols of F1, 6P2, per mg of the protein, cleaved within 1 minute (µmol/min/mg protein).

Reaction liquid 200 µl: 0.25 mM tris HCl buffer (pH 8.0), 0.15 M NaCl, 0.5 mM F1, 6P2 (from Sigma), human 35 kd protein, human liver TIM (500 µg/ml), rabbit skeletal muscle G3PDH (8 units/ml, from Sigma), 0.3 mM NADH (from Nakarai).

For comparison, a commercial product aldolase, Sigma's rabbit skeletal muscle aldolase (A-type aldolase), and an enzyme-free system were tested in the same manner. The results are shown in Table 2. The activity data confirm that the human 35 kd protein has an aldolase activity.

TABLE 2

Enzymatic Activity in Aldol Cleavage Reaction

| Additive | Aldolase Activity (µmol/min/mg protein) |
|---|---|
| Enzyme-free system | below detection limit |
| Sigma's commercial product aldolase | 0.278 |
| Human 35 kd protein | 0.0034 |

INDUSTRIAL APPLICABILITY

The present invention provides a protein that participates in regulation of sugar production, and a polynucleotide that encodes it.

Since the invention provides a screening method for a compound that participates in regulation of sugar production, it makes it possible to evaluate compounds participating in regulation of sugar production.

Further, the invention provides a medicine for treatment or prevention of diabetes, that contains the compound participating in regulation of sugar production.

The invention claimed is:

1. An isolated polynucleotide:
   which consists of a coding region for a polypeptide, wherein said polypeptide binds to WF00144 and has a molecular weight of about 35 kD; and
   said polynucleotide has at least 96% sequence identity to SEQ ID NO: 1, or which hybridizes to the complement of SEQ ID NO: 1 under stringent conditions, wherein stringent conditions comprise washing in 0.1×SSC and 0.1% SDS at 68° C.

2. The isolated polynucleotide of claim 1, which has at least 96% sequence identity to SEQ ID NO: 1.

3. The isolated polynucleotide of claim 1, which hybridizes to the complement of SEQ ID NO: 1 under stringent conditions, wherein stringent conditions comprising washing in 0.1×SSC and 0.1% SDS at 68° C.

4. The isolated polynucleotide of claim 1, which encodes a polypeptide comprising SEQ ID NO: 2.

5. The isolated polynucleotide of claim 1, which consists of SEQ ID NO: 1.

6. The isolated polynucleotide of claim 1, wherein said encoded polypeptide has at least 96% sequence identity to SEQ ID NO: 2.

7. The isolated polynucleotide of claim 1, which encodes a polypeptide in which one to five of the amino acid residues in SEQ ID NO: 2 are different than the corresponding amino acids in SEQ ID NO: 2.

8. An expression vector comprising the polynucleotide of claim 1, which expresses a polypeptide that binds to WF00144 and has a molecular weight of about 35 kDa.

9. A transformant comprising the polynucleotide of claim 1.

10. The full complement of the polynucleotide of claim 1.

11. The isolated polynucleotide of claim 1, further consisting of at its 5' end an oligonucleotide encoding histidine, lysine or arginine.

12. A viral vector comprising the isolated polynucleotide of claim 1.

13. A liposome comprising the isolated polynucleotide of claim 1.

14. A method for making a polypeptide that binds to WF00144, comprising culturing the transformant of claim 9 under conditions suitable for production of a polypeptide that binds to WF00144, and rec

SEQUENCE LISTING

<160> NUMBER OF SEQ ID NOS: 9

<210> SEQ ID NO 1
<211> LENGTH: 1061
<212> TYPE: DNA
<213> ORGANISM: Homo sapiens

<400> SEQUENCE: 1

```
gaagtctatg ctgggtcccc aagtctggtc ttctgtgagg caggggctaa gcaggagctt    60
gtccaggaat gtgggggtct gggcctcagg ggaggggaag aaggtggaca ttgcgggtat   120
ctaccccctg tgaccacccc cttcactgcc actgcagagg tggactatgg ggaaactgga   180
ggagaatctg cacaaactgg gcaccttccc cttccgaggc ttcgtggtcc agggctccaa   240
tggcgagttt cctttcctga ccagcagtga gcgcctcgag gtggtgagcc gtgtgcgcca   300
ggccatgccc aagaacaggc tcctgctagc tggctccgga tgcgagtcca ctcaagccac   360
agtggagatg accgtcagca tgcccaggt cggggctgac gcggccatgg tggtgacccc   420
ttgctactat cgtggccgca tgagcagtgc ggccctcatt caccactaca ccaaggttgc   480
tgatctctct ccaatccctg tggtgctgta cagtgtccca gccaacacag ggctggacct   540
gcctgtggat gcagtggtca cgcttttccca gcacccgaat attgtgggca tgaaggacag   600
cggtggtgat gtgaccagga ttgggctgat tgttcacaag accaggaagc aggattttca   660
ggtgttggct ggatcggctg gctttctgat ggccagctat gccttgggag ctgtgggggg   720
cgtctgcgcc ctggccaatg tcctgggggc tcaggtgtgc cagctggagc gactgtgctg   780
cacggggcaa tgggaagatg cccagaaact gcagcaccgc tcattgagc caaacgctgc   840
ggtgacccgg cgctttggga tcccagggct gaagaaaatc atggactggt ttggctacta   900
tggaggcccc tgccgcgccc ccttgcagga gctgagcccc gctgaggagg aggcactgcg   960
catggatttc accagcaacg gctggctctg agggcaggca gggtccatgg ctggcctgag  1020
cccatctcag cctcctgcct tgcacttgca gcctgaattc                        1061
```

<210> SEQ ID NO 2
<211> LENGTH: 327
<212> TYPE: PRT
<213> ORGANISM: Homo sapiens

<400> SEQUENCE: 2

```
Met Leu Gly Pro Gln Val Trp Ser Ser Val Arg Gln Gly Leu Ser Arg
1               5                   10                  15

Ser Leu Ser Arg Asn Val Gly Val Trp Ala Ser Gly Glu Gly Lys Lys
            20                  25                  30

Val Asp Ile Ala Gly Ile Tyr Pro Pro Val Thr Thr Pro Phe Thr Ala
        35                  40                  45

Thr Ala Glu Val Asp Tyr Gly Lys Leu Glu Glu Asn Leu His Lys Leu
    50                  55                  60

Gly Thr Phe Pro Phe Arg Gly Phe Val Val Gln Gly Ser Asn Gly Glu
65                  70                  75                  80

Phe Pro Phe Leu Thr Ser Ser Glu Arg Leu Glu Val Val Ser Arg Val
                85                  90                  95

Arg Gln Ala Met Pro Lys Asn Arg Leu Leu Leu Ala Gly Ser Gly Cys
            100                 105                 110

Glu Ser Thr Gln Ala Thr Val Glu Met Thr Val Ser Met Ala Gln Val
        115                 120                 125
```

```
Gly Ala Asp Ala Ala Met Val Val Thr Pro Cys Tyr Tyr Arg Gly Arg
    130                 135                 140

Met Ser Ser Ala Ala Leu Ile His His Tyr Thr Lys Val Ala Asp Leu
145                 150                 155                 160

Ser Pro Ile Pro Val Val Leu Tyr Ser Val Pro Ala Asn Thr Gly Leu
                165                 170                 175

Asp Leu Pro Val Asp Ala Val Val Thr Leu Ser Gln His Pro Asn Ile
            180                 185                 190

Val Gly Met Lys Asp Ser Gly Gly Asp Val Thr Arg Ile Gly Leu Ile
        195                 200                 205

Val His Lys Thr Arg Lys Gln Asp Phe Gln Val Leu Ala Gly Ser Ala
    210                 215                 220

Gly Phe Leu Met Ala Ser Tyr Ala Leu Gly Val Gly Gly Val Cys
225                 230                 235                 240

Ala Leu Ala Asn Val Leu Gly Ala Gln Val Cys Gln Leu Glu Arg Leu
                245                 250                 255

Cys Cys Thr Gly Gln Trp Glu Asp Ala Gln Lys Leu Gln His Arg Leu
            260                 265                 270

Ile Glu Pro Asn Ala Ala Val Thr Arg Arg Phe Gly Ile Pro Gly Leu
        275                 280                 285

Lys Lys Ile Met Asp Trp Phe Gly Tyr Tyr Gly Pro Cys Arg Ala
    290                 295                 300

Pro Leu Gln Glu Leu Ser Pro Ala Glu Glu Ala Leu Arg Met Asp
305                 310                 315                 320

Phe Thr Ser Asn Gly Trp Leu
                325

<210> SEQ ID NO 3
<211> LENGTH: 1017
<212> TYPE: DNA
<213> ORGANISM: Rattus sp.

<400> SEQUENCE: 3
cgggatccat gctgggcccc caaatctggg cctccatgag gcaggggctg agcaggggct    60
tgtctaggaa cgtgaagggg aagaagatag acattgccgg catctaccca cccgtgacca   120
ccccattcac cgccaccgca gaagtagact atgggaaact ggaagagaac ctgaacaaac   180
tggccgcctt ccccttttcga ggcttcgtgg tccagggctc tactggagag tttccattcc   240
tgaccagcct tgagcgccta gaggtggtga gccgagtgcg ccaggccata cccaaggaca   300
agctcctgat agccggctct ggctgcgagt ccacgcaagc cacagtagag atgactgtca   360
gcatggctca ggtgggtgct gatgccgcca tggtggtgac cccttgttac tatcgcggcc   420
gcatgaacag cgctgccctc attcaccact acaccaaggt tgctgatctt tctccaatcc   480
cggtggtgct gtacagtgtc ccaggcaaca cgggtctaga gctgcctgtg gatgccgtgg   540
tcacattgtc tcagcaccca aatatcattg gcttgaagga cagtggtgga gatgtgacca   600
ggactgggct gattgttcac aagaccagca agcaggattt ccaggtgttg gctgggtcag   660
ttggcttcct cctggccagc tatgctgtgg gagctgttgg gggcatatgt ggcctggcca   720
atgtcttggg ggcccaggtg tgccagctgg agagactctg cctcacaggg caggggaag    780 ctgcccagag actgcagcac cgcctcatcg agcccaacac tgcggtgacc cggcgctttg   840
gaataccagg gctgaagaaa accatggact ggtttggcta ctatggaggt ccctgccgtg   900
cccccttgca ggagttgagc ccctcagagg aagaggcgct tcgcttggat ttcagcaaca   960
```
atggctggct ttaatgacaa gcgggggaca cctggtctga gctgtctcag aattccg    1017

<210> SEQ ID NO 4
<211> LENGTH: 321
<212> TYPE: PRT
<213> ORGANISM: Rattus sp.

<400> SEQUENCE: 4

```
Met Leu Gly Pro Gln Ile Trp Ala Ser Met Arg Gln Gly Leu Ser Arg
1               5                   10                  15

Gly Leu Ser Arg Asn Val Lys Gly Lys Lys Ile Asp Ile Ala Gly Ile
            20                  25                  30

Tyr Pro Pro Val Thr Thr Pro Phe Thr Ala Thr Ala Glu Val Asp Tyr
        35                  40                  45

Gly Lys Leu Glu Glu Asn Leu Asn Lys Leu Ala Ala Phe Pro Phe Arg
    50                  55                  60

Gly Phe Val Val Gln Gly Ser Thr Gly Glu Phe Pro Phe Leu Thr Ser
65                  70                  75                  80

Leu Glu Arg Leu Glu Val Val Ser Arg Val Arg Gln Ala Ile Pro Lys
                85                  90                  95

Asp Lys Leu Leu Ile Ala Gly Ser Gly Cys Glu Ser Thr Gln Ala Thr
            100                 105                 110

Val Glu Met Thr Val Ser Met Ala Gln Val Gly Ala Asp Ala Ala Met
        115                 120                 125

Val Val Thr Pro Cys Tyr Tyr Arg Gly Arg Met Asn Ser Ala Ala Leu
    130                 135                 140

Ile His His Tyr Tyr Lys Val Ala Asp Leu Ser Pro Ile Pro Val Val
145                 150                 155                 160

Leu Tyr Ser Val Pro Gly Asn Thr Gly Leu Glu Leu Pro Val Asp Ala
                165                 170                 175

Val Val Thr Leu Ser Gln His Pro Asn Ile Ile Gly Leu Lys Asp Ser
            180                 185                 190

Gly Gly Asp Val Thr Arg Thr Gly Leu Ile Val His Lys Thr Ser Lys
        195                 200                 205

Gln Asp Phe Gln Val Leu Ala Gly Ser Val Gly Phe Leu Leu Ala Ser
    210                 215                 220

Tyr Ala Val Gly Ala Val Gly Gly Ile Cys Gly Leu Ala Asn Val Leu
225                 230                 235                 240

Gly Ala Gln Val Cys Gln Leu Glu Arg Leu Cys Leu Thr Gly Gln Gly
                245                 250                 255

Glu Ala Ala Gln Arg Leu Gln His Arg Leu Ile Glu Pro Asn Thr Ala
            260                 265                 270

Val Thr Arg Arg Phe Gly Ile Pro Gly Leu Lys Lys Thr Met Asp Trp
        275                 280                 285

Phe Gly Tyr Tyr Gly Gly Pro Cys Arg Ala Pro Leu Gln Glu Leu Ser
    290                 295                 300

Pro Ser Glu Glu Glu Ala Leu Arg Leu Asp Phe Ser Asn Asn Gly Trp
305                 310                 315                 320

Leu
```

<210> SEQ ID NO 5
<211> LENGTH: 202
<212> TYPE: PRT
<213> ORGANISM: Rattus sp.
<220> FEATURE:

<221> NAME/KEY: misc_feature
<222> LOCATION: (165)..(165)
<223> OTHER INFORMATION: Xaa can be any naturally occurring amino acid

<400> SEQUENCE: 5

```
Gly Arg Met Asn Ser Ala Ala Leu Ile His His Tyr Thr Lys Val Ala
1               5                   10                  15

Asp Leu Ser Pro Ile Pro Val Val Leu Tyr Ser Val Pro Gly Asn Thr
            20                  25                  30

Gly Leu Glu Leu Pro Val Asp Ala Val Val Thr Leu Ser Gln His Pro
        35                  40                  45

Asn Ile Ile Gly Leu Lys Asp Ser Gly Gly Asp Val Thr Arg Thr Gly
    50                  55                  60

Leu Ile Val His Lys Thr Ser Lys Gln Asp Phe Gln Val Leu Ala Gly
65                  70                  75                  80

Ser Val Gly Phe Leu Leu Ala Ser Tyr Ala Val Gly Ala Val Gly Gly
                85                  90                  95

Ile Val Gly Leu Ala Asn Val Leu Gly Ala Gln Val Cys Gln Leu Glu
            100                 105                 110

Arg Leu Cys Leu Thr Gly Gln Gly Glu Ala Ala Gln Arg Leu Gln His
        115                 120                 125

Arg Leu Ile Glu Pro Asn Thr Ala Val Thr Arg Arg Phe Gly Ile Pro
    130                 135                 140

Gly Leu Lys Lys Thr Met Asp Trp Phe Gly Tyr Tyr Gly Gly Pro Cys
145                 150                 155                 160

Arg Ala Pro Leu Xaa Glu Leu Ser Pro Ser Glu Glu Ala Leu Arg
                165                 170                 175

Leu Asp Phe Ser Asn Asn Gly Trp Leu Gln Ala Gly Asp Thr Trp Ser
            180                 185                 190

Glu Leu Ser Gln Thr Leu Val Pro Thr Val
        195                 200
```

<210> SEQ ID NO 6
<211> LENGTH: 30
<212> TYPE: DNA
<213> ORGANISM: Rattus sp.

<400> SEQUENCE: 6
cgggatccaa tgctgggccc ccaaatctgg          30

<210> SEQ ID NO 7
<211> LENGTH: 24
<212> TYPE: DNA
<213> ORGANISM: Rattus sp.

<400> SEQUENCE: 7
cggaattctg agacagctca gacc          24

<210> SEQ ID NO 8
<211> LENGTH: 29
<212> TYPE: DNA
<213> ORGANISM: Homo sapiens

<400> SEQUENCE: 8
gaagatctat gctgggtccc caagtctgg          29

<210> SEQ ID NO 9
<211> LENGTH: 30
<212> TYPE: DNA

```
<213> ORGANISM: Homo sapiens

<400> SEQUENCE: 9
ggaattcagg ctgcaagtgc aaggcaggag                                        30
```